US011083139B2

(12) United States Patent
Bitetti

(10) Patent No.: US 11,083,139 B2
(45) Date of Patent: Aug. 10, 2021

(54) HIGH-GROWTH SYSTEM AND METHOD FOR CULTIVATING AUTOFLOWERING CANNABIS

(71) Applicant: Blazing Bits, LLC, Woonsocket, RI (US)

(72) Inventor: Vincent J. Bitetti, Thousand Oaks, CA (US)

(73) Assignee: Blazing Bits, LLC, Woonsocket, RI (US)

( * ) Notice: Subject to any disclaimer, the term of this patent is extended or adjusted under 35 U.S.C. 154(b) by 145 days.

(21) Appl. No.: 16/133,242

(22) Filed: Sep. 17, 2018

(65) Prior Publication Data

US 2019/0082612 A1   Mar. 21, 2019

Related U.S. Application Data

(60) Provisional application No. 62/559,327, filed on Sep. 15, 2017, provisional application No. 62/614,743, filed on Jan. 8, 2018.

(51) Int. Cl.
*A01H 6/28* (2018.01)
*A01G 9/14* (2006.01)
(Continued)

(52) U.S. Cl.
CPC .......... *A01G 7/045* (2013.01); *A01G 9/1438* (2013.01); *A01G 9/16* (2013.01); *A01G 9/246* (2013.01); *A01G 31/02* (2013.01); *A01H 6/28* (2018.05)

(58) Field of Classification Search
USPC .............. 47/58.1 LS, 17, 29.5, 66.7, DIG. 6
See application file for complete search history.

(56) References Cited

U.S. PATENT DOCUMENTS 3,336,773 A * 8/1967 Oechslin ............. G07F 9/105
70/337
4,543,744 A * 10/1985 Royster .................. A01G 9/00
47/17

(Continued)

FOREIGN PATENT DOCUMENTS

DE        69014353 D1        1/1995
DE    202017101739 U1        5/2017
(Continued)

OTHER PUBLICATIONS

Ideas For Grow Room Dividers, Feb. 26, 2017, retrieved from internet [https://www.thcfarmer.com/threads/ideas-for-grow-room-dividers.87182/] 15 pages.*

*Primary Examiner* — Andrea M Valenti
(74) *Attorney, Agent, or Firm* — MG Miller Intellectual Property Law LLC

(57) ABSTRACT

High-growth plant cultivation techniques are provided that create efficient, optimized growing conditions, including a high concentration of photosynthetically active radiation ("PAR") in terms of photon flux density, and with extremely low heat. In some aspects of the invention, these techniques comprise a specialized growth chamber and a control system that promote an enhanced level of growth, particularly for autoflowering cannabis. In addition, aspects of the invention create an accessible, user-friendly, aesthetically pleasing new type of display for a plant, ideal for cultivating cannabis and, in particular, autoflowering cannabis. The unique combination of techniques set forth in the invention create high yields of cannabis plant matter (up to 3 or 4 times greater than other methods) in substantially less time (just 60 days from seed to harvest).

9 Claims, 2 Drawing Sheets

(51) Int. Cl.
  *A01G 31/02* (2006.01)
  *A01G 9/16* (2006.01)
  *A01G 7/04* (2006.01)
  *A01G 9/24* (2006.01)

(56) References Cited

U.S. PATENT DOCUMENTS

| | | | |
|---|---|---|---|
| 6,536,157 B2 * | 3/2003 | Wijbenga | A01G 9/16 |
| | | | 47/17 |
| 6,725,598 B2 | 4/2004 | Yoneda et al. | |
| 7,823,324 B2 * | 11/2010 | Townsley | A01G 9/16 |
| | | | 47/17 |
| 8,443,546 B1 * | 5/2013 | Darin | A01G 31/02 |
| | | | 47/59 R |
| 8,984,806 B2 * | 3/2015 | Uchiyama | A01G 9/24 |
| | | | 47/17 |
| 9,101,096 B1 | 8/2015 | Lewis | |
| 9,591,815 B2 | 3/2017 | Fujiyama et al. | |
| 9,727,048 B2 | 8/2017 | So | |
| 9,844,518 B2 * | 12/2017 | Lowe | A01G 22/00 |
| 9,907,236 B2 * | 3/2018 | Kamp | A01G 9/246 |
| D829,471 S * | 10/2018 | Fortmann | D6/661 |
| 10,455,777 B1 * | 10/2019 | Dennison | A01G 9/246 |
| 10,499,574 B2 * | 12/2019 | Lu | G08B 21/18 |
| 10,552,951 B2 * | 2/2020 | Barrasso | G06T 7/11 |
| 2001/0047618 A1 * | 12/2001 | Fang | A01G 7/045 |
| | | | 47/65.5 |
| 2005/0178058 A1 * | 8/2005 | Rudolph | A01G 9/16 |
| | | | 47/60 |
| 2009/0025287 A1 * | 1/2009 | Lee | A01G 9/246 |
| | | | 47/17 |
| 2014/0026474 A1 * | 1/2014 | Kulas | A01G 9/02 |
| | | | 47/1.7 |
| 2014/0115958 A1 * | 5/2014 | Helene | A01G 9/24 |
| | | | 47/17 |
| 2015/0000191 A1 | 1/2015 | Nagadome et al. | |
| 2015/0089867 A1 | 4/2015 | Abbott et al. | |
| 2016/0157439 A1 * | 6/2016 | Greene | A01G 9/249 |
| | | | 47/17 |
| 2016/0183477 A1 | 6/2016 | Kao et al. | |
| 2016/0184237 A1 * | 6/2016 | Lowe | A61K 36/185 |
| | | | 514/733 |
| 2018/0007845 A1 * | 1/2018 | Martin | A01G 31/06 |
| 2018/0184602 A1 * | 7/2018 | Ofir | A01G 7/045 |

FOREIGN PATENT DOCUMENTS

| | | |
|---|---|---|
| JP | 2013162747 A | 8/2013 |
| JP | 2014030377 A2 | 2/2014 |
| JP | 2017507666 A | 3/2017 |
| KR | 101261301 B1 | 4/2013 |
| WO | 2016180017 A1 | 11/2016 |

* cited by examiner

HIGH-GROWTH SYSTEM AND METHOD FOR CULTIVATING AUTOFLOWERING CANNABIS

CLAIM OF PRIORITY

This application claims priority to U.S. Provisional Patent Application No. 62/559,327 entitled "Autoflower Grow Box", filed on Sep. 15, 2017, and to U.S. Provisional Patent Application No. 62/614,743 entitled "High-Growth System and Method for Cultivating Autoflowering Cannabis", filed on Jan. 8, 2018.

NOTICE OF COPYRIGHTS AND TRADE DRESS

A portion of the disclosure of this patent document contains material which is subject to copyright or trade dress protection. This patent document may show and/or describe matter that is or may become trade dress of the owner. The copyright and trade dress owner has no objection to the facsimile reproduction by anyone of the patent disclosure, as it appears in the Patent and Trademark Office patent files or records, but otherwise reserves all copyright and trade dress rights whatsoever.

FIELD OF THE EMBODIMENTS

The present invention relates to the apparatuses and methods for cultivating cannabis plants and, more specifically, autoflowering cannabis plants.

BACKGROUND

"Autoflowering cannabis" refers to varieties of the cannabis genus of flowering plants that switch from a vegetative growth stage to a flowering stage based on age, rather than length-of day. Conventional varieties of cannabis switch to the flowering stage by measuring the ratio of light to dark hours, to flower according to the seasons.

Varieties of autoflowering cannabis include unique cross-breeding products of one or more species of cannabis, notably, *Cannabis ruderalis* (thought to be derived from *Cannabis sativa*) and are potentially adapted to colder climates and rougher soil of Europe. Originally, feral cannabis varieties were marked by low tetrahydrocannabinol ("THC") levels, and were therefore of limited use for recreational and medical purposes. Modern autoflowering cannabis varieties now include high-THC varieties, are capable of high growth rates, and are derived from cross-breeding *Cannabis ruderalis* with *Cannabis sativa* or *Cannabis indica*. Autoflowering cannabis also tends to exhibit a high cannabidiol ("CBD") level, which is medically useful in the treatment of anxiety and epilepsy, for example.

However, promising as they are, autoflowering cannabis varieties can create unique new challenges for farmers, and in particular to potential, future amateur, home-based farmers, and at-home hobbyists ("DIY consumers") if and when at-home growing is legalized for them in their jurisdictions. Although a more rapid rate of growth is possible with autoflowering cannabis, the greater light exposure (and its attendant heat) to fuel that growth creates special risks such as dehydration and degradation of the plant (i.e. "burnout") and infestations of mites and other plant "sucking" insects such as common aphids-rendering the medicine generally unusable and greatly diminishing yield. These risks are realized when conventional growth lamps and methods, intended for growing conventional cannabis, are used on autoflowering cannabis, which has a shorter stature, and more sparse foliage. Based on these factors, it is particularly difficult to control these types of risks.

Disclosed is a system and method that protects and enhances the growth of autoflowering cannabis. In particular, a system delivering an ideal amount of photosynthetically active radiation ("PAR"), ideal soil and nutrient conditions, soil PH, airflow, and hydration for autoflowering cannabis, "self-pruning" grow containers (cloth pots for example), while also creating a convenient, confined (yet easily-accessible), and pleasant display of an autoflowering cannabis plant.

Applicant also notes that some of the disclosures set forth as background do not relate exclusively to prior art and the state of the art in the field(s) of the invention, and should not be construed as an admission with respect thereto.

While these units may be suitable for the particular purpose employed, or for general use, they would not be as suitable for the purposes of the present disclosure as disclosed hereafter.

In the present disclosure, where a document, act, or item of knowledge is referred to or discussed, this reference or discussion is not an admission that the document, act, item of knowledge, or any combination thereof that was known at the priority date, publicly available, known to the public, part of common general knowledge or otherwise constitutes prior art under the applicable statutory provisions; or is known to be relevant to an attempt to solve any problem with which the present disclosure is concerned.

While certain aspects of conventional technologies have been discussed to facilitate the present disclosure, no technical aspects are disclaimed. It is contemplated that the claims may encompass one or more of the conventional technical aspects discussed herein.

SUMMARY

In one embodiment of the present invention, a system for aiding the cultivation of autoflowering cannabis is disclosed. This embodiment features a "cocoon-like" chamber having a front end, a rear end, a top side, a bottom side, a right side, a left side, and in some models, a plurality of walls extending therebetween. These walls are equipped with at least one air intake and at least one air exhaust port. Preferably, all of the exhaust ports are equipped with a carbon-based filter and the air intakes are equipped with an anti-pest mesh filter. The bottom side of the chamber is configured to support an autoflowering cannabis plant housed in a cloth pot. Note that hydroponic and aeroponic systems are not suitable for use with the system of the present invention. The interior of the chamber is also equipped with a light array. This light array is preferably made up of a plurality of light-emitting diodes which will shine from the top side of the chamber towards the bottom side. The chamber also is equipped with a plurality of fans which are configured to create airflow within the chamber. Some embodiments of the chamber may feature a glass wall extending across the front side of the chamber, and other embodiments feature a median which splits the chamber into two sub-chambers allowing for two plants to be cultivated, even if those plants are of different strains.

The light array is configured to produce light within the photosynthetically active radiation ranges of autoflowering cannabis, and preferably to a greater degree than light outside the photosynthetically active radiation ranges for autoflowering cannabis. In a highly preferred embodiment, the light array emits light at 430 and 662 nanometers and/or 452 and 652 nanometers. In another embodiment, the light array creates photosynthetically active radiation of at least 1,500 mol m$^{-2}$s$^{-1}$ and consumes between 100 and 200 Watts of power.

Further, high-growth plant cultivation techniques are provided that create efficient and optimized growing conditions, including Low Stress Training (LST), a "self pruning" cloth grow pot, a high concentration of photosynthetically active radiation ("PAR"), and low heat. In some aspects of the invention, these techniques comprise a specialized growth chamber and a system that promotes an enhanced level of growth for autoflowering cannabis.

In some aspects, the system selectively yields a high level of PAR within the growth chamber with an array of light-emitting diodes ("LEDs"), to cultivate a plant held within said growth chamber. Each diode is optimized to cast light preferentially at the "A"-type absorption peaks for chlorophyll, namely, light having wavelengths of 430 and 662 nanometers. However, in some embodiments, the LEDs are also or alternatively, optimized to preferably cast light preferentially in the "B"-type absorption peaks for chlorophyll, namely, light having wavelengths 453 and 652 nanometers. Preferably, a plurality of LEDs, ranging from 60 to 150 LEDs, are used in each chamber, but other numbers of LEDs, in addition, or alternatively, may be used in some embodiments of the invention.

In other aspects of the invention, the growth chamber is an airtight enclosure adapted to hold and cultivate an autoflowering cannabis plant. The airtight enclosure may comprise both an intake subsystem and an exhaust subsystem preferably at or about the top of the growth chamber, each of which is separately filtered (if the embodiment has dual-chambers), preferably with an activated carbon-based filter. However, a wide array of possible filters, filtrates, types of filtration, and devices may also, or in addition, be used in various embodiments of the invention, which will be understood by a person of ordinary skill in the art. Also, preferably or in some embodiments of the system, the chamber comprises waterproof materials or surfaces, such as fiberglass or plastic surfaces. The inside of the chamber may be "flat" or "satin" white water-resistant, easy to clean paint, epoxy or other suitable interior finishes.

Also, preferably, the system incorporates and creates optimized growing conditions within the growth chamber, including the following parameters:

Light intensity within the chamber is controlled to preferentially concentrate on "A"-type light absorption peaks for chlorophyll (and/or, in some embodiments, for "B"-type light absorption peaks for chlorophyll), and with a high level of PAR for autoflowering cannabis. Further the light intensity will be generated along with a low level of heat (using low-voltage, high PAR LED array, namely creating over 1,500 micromoles, or mol m$^{-2}$s$^{-1}$, ("micromoles") of PAR, and even more preferably between 2,000 and 2,500 micromoles of PAR with a wattage for the lighting subsystem comprised in the system of between 150 and 200 watts. An LED light array is used in many preferred embodiments and is suspended closer to the top growth ("canopy") of the cultivated plant than in prior art arrangements. Even more preferably, the LEDs of the light array are as close as 3 to 4 inches from the canopy of the cultivated autoflowering cannabis plant. In some embodiments, the LEDs can be suspended closer or further away (e.g. 6 inches).

A pot with organic fertilizing soil, preferably with a pH of about 6.2 to 6.8, and even more preferably, with a maximum pH of 6.8, and preferably to which beneficial microbes have been added to enhance the nutrient profile of the soil;

Continued periodic hydration with purified water, preferably with an approximately neutral pH, or a slightly basic pH, or in some embodiments, a slightly acidic pH. However, preferably, the pH of water provided to the cultivated plant is between 5.5 to 5.7. Preferably, for an average-size autoflowering cannabis plant, depending upon the strain of autoflowering cannabis used, approximately ½ gallon of purified water every 2 to 4 days for a total of between 60 and 90 days is required.

Regular temperature control can be achieved, by placing the system within a room having a moderate temperature of between 65 and 78 degrees Fahrenheit.

The parameters above are implemented in related methods for using the chamber as well.

The unique combination of techniques set forth in the invention create high yields of cannabis plant matter (up to 3 or 4 times greater than other methods) in substantially less time (just 60 days from seed to harvest) than ordinarily expected.

The present disclosure addresses at least one of the foregoing disadvantages. However, it is contemplated that the present disclosure may prove useful in addressing other problems and deficiencies in a number of technical areas. Therefore, the claims should not necessarily be construed as limited to addressing any of the particular problems or deficiencies discussed hereinabove. To the accomplishment of the above, this disclosure may be embodied in the form illustrated in the accompanying drawings. Attention is called to the fact, however, that the drawings are illustrative only. Variations are contemplated as being part of the disclosure.

Implementations may include one or a combination of any two or more of the aforementioned features.

These and other aspects, features, implementations, and advantages can be expressed as methods, apparatuses, systems, components, program products, business methods, and means or steps for performing functions, or some combination thereof.

Other features, aspects, implementations, and advantages will become apparent from the descriptions, the drawings, and the claims.

BRIEF DESCRIPTION OF THE PREFERRED EMBODIMENTS

In the drawings, like elements are depicted by like reference numerals. The drawings are briefly described as follows.

The present disclosure now will be described more fully hereinafter with reference to the accompanying drawings, which show various example embodiments. However, the present disclosure may be embodied in many different forms and should not be construed as limited to the example embodiments set forth herein. Rather, these example embodiments are provided so that the present disclosure is thorough, complete, and fully conveys the scope of the present disclosure to those skilled in the art. In fact, it will be apparent to those skilled in the art that various modifications and variations can be made in the present invention without departing from the scope or spirit of the invention.

DETAILED DESCRIPTION OF THE PREFERRED EMBODIMENTS

Figure 1:
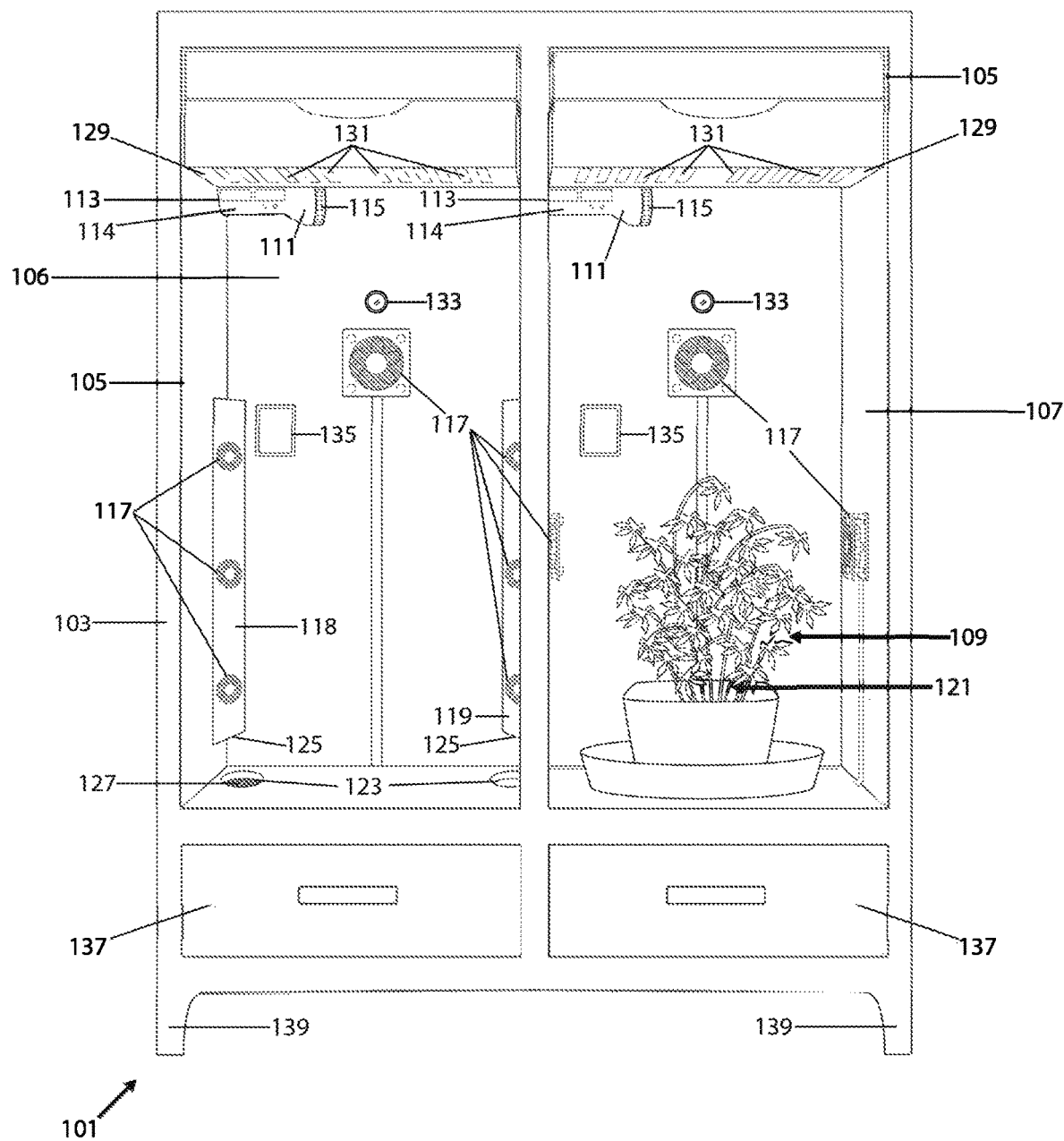
FIG. 1 is a front perspective view of an exemplary system for aiding the cultivation of autoflowering cannabis, in accordance with aspects of the present invention.

FIG. 1 is a front perspective view of an exemplary system 101 for aiding the cultivation of autoflowering cannabis, in accordance with aspects of the present invention. System 101 comprises a rigid outer housing 103, and at least one front-facing port(s) 105, displaying at least one airtight, interior growth chamber(s), such as the examples shown in chamber(s) 106 and 107, each of which is configured for holding, cultivating and viewing at least one autoflowering cannabis plant, such as the example shown in chamber 107, as plant 109. In various embodiments, the system 101 is equipped with a main front door which is equipped with a magnetic lock system. Preferably, the magnetic lock system also includes a child-proof magnetic lock with matching unlocking "magnetic bob" providing additional safety benefits.

Among other advantages, system 101 comprises an airflow management subsystem, for creating an ideal airflow for an autoflowering cannabis plant, cultivated within the growth chamber(s), such as chamber(s) 106 and 107. The airflow management subsystem, and system 101 as a whole, includes at least one higher capacity main air exhaust fan(s) 111, preferably with a capacity of within the range of 150 to 200 cubic feet per minute ("CFM") of air movement. Preferably, at least one, main exhaust fan(s) 111 is located at or about the top end of the chamber(s), 106 and 107. Also preferably, the main exhaust fan(s) 111 is located as pictured, approximately at the top and back of the chamber(s) 106 and 107 and is abutting or integrated with an exhaust port(s) (not pictured, but approximately at the locations shown by 113), which abuts a venting tube 114, in turn, connected and integral with main exhaust fan(s) 111, which itself, abuts a carbon-based or other deodorizing filter 115, configured to filter all air pulled out of the chamber(s) 106 and 107 by main exhaust fan(s) 111. Also, preferably, the carbon-based or other deodorizing filters 115 removes substantially all odors that might irritate or otherwise be noticed by occupants of the room in which system 101 is placed. It should be understood that, although certain configurations, numbers, and orders of the above elements are pictured, a number of additional configurations, numbers, and orders of the elements of the invention may be used, alternatively or in addition to that which is pictured. Such other arrangements of the elements of the invention will be readily apparent to those of ordinary skill in the art. For example, the deodorizing filters 115 are shown abutting air fan(s) 111, and may alternatively be positioned covering exhaust port(s) 113, and/or within venting tube 114, or at any other position guaranteeing effective filtering of airflow out of the chamber (s) 106 and 107.

In some embodiments, a plurality of internal air circulation fans, such as the examples pictured as 117, may also be comprised in the airflow management subsystem of system 101 and located within the chamber(s), 106 and 107. Preferably, this is at or about the lower regions of the chambers, vertically. For example, the banks 118 and 119 of such circulation fans 117 is pictured, and are placed within exemplary cultivation chamber 106, at or about the lower rear corners, being configured to aid in cooling a cultivated plant housed within chamber 106. In an alternative embodiment, pictured within chamber 107, circulation fans 117 are not grouped in banks but instead are placed along the opaque walls and/or corners of the chamber. Of course, a wide variety of alternative numbers and positions of circulation fans 117 may be used, alternatively or in addition to the configurations pictured, while still carrying out aspects of the present invention. Circulation fans 117 also subject the cultivated plant to air movement by simulating wind, and strengthening the exposed stems of an autoflowering cannabis plant held within the chamber (especially the main stems, such as those pictured as 121 of exemplary plant 109). Preferably, the airflow management subsystem is configured to create airflow directly toward the at least partially exposed stems of an autoflowering cannabis plant. For example, with fans being placed as pictured and described herein, or by otherwise being placed and aimed at the level of exposed plant stems of a maturing or mature autoflowering cannabis plant (e.g., aimed at a region just above the top rim of the plant's pot, or within 4 inches above the rim of the plant's pot).

Each of the plurality of internal air circulation fans 117 preferably has a lower capacity than the main exhaust fan(s) 111, such as a capacity of roughly between 30 and 60 CFM, and even more preferably, has a capacity of roughly 40 to 60 CFM of air movement. As mentioned above, the internal circulation fans 117 are preferably placed at or about the bottom, middle, and top of chamber(s) 106 and 107, moving cooler air around, about and toward the cultivated plant's main stems 121. Also preferably, the air circulation fans 117 are placed such that air abuts both sides of each of the fans 117, permitting optimal airflow. More preferably, as pictured, the circulation fans 117 are placed across from one another at or about the lower corners of the chamber(s) 106 and 107, and are facing inward, as pictured in chamber 106.

Preferably, air circulation fans 117 are not connected directly with an air intake or exhaust outlet from the chamber(s) 106 and 107. However, at least some of circulation fans 117 are placed near, at or about at least one passive air intake(s) 123, each of which intake(s) 123 are configured to take in air from outside the chamber(s) 106 and 107, and each of which intake(s) is preferably placed at, near or about the bottom end of chamber(s) 106 and 107. Also preferably, circulation fans 117 are arranged in banks of two or more circulation fans, as pictured in chamber 106, each with a common internal air intake(s) 125, at or about the bottom of the chamber 106 and 107, and near the chamber's passive air intake(s) 123. Preferably, a plurality of air intake(s) 123 and air intake(s) 125 are included, and, also preferably, each of air intake(s) 123 are placed with approximately ½ of their profile directly under an air intake 125, and ½ of their profile directly outside of it, as pictured. Each of the air intake(s) 125 may be any suitable size permitting airflow, but preferably are approximately 3 to 4 inches wide in diameter. Further, as with exhaust port 113, the air intake(s) 125 are sealed by and/or coupled with or covered by an intake filter, such as the example pictured as 127, which is a micro screen or other mesh-based (such as filter plate covers), or another suitable filter type known in the art and capable of filtering approximately micron-sized particles, among other things such as small insects, pet hair, dust, and dust mites. The exhaust port(s) 113 also may be any suitable size permitting air flow, but are also preferably 4 to 6 inches in diameter, or larger. In some alternative embodiments, such as that pictured in chamber 107, the air intakes may abut the circulation fans 117, opening onto the air exterior to system 101 through holes in the walls of chamber 107, rather than holes in the floor, as pictured in examples 123.

In combination, the higher capacity main exhaust fan(s) 111, the plurality of internal air circulation fans 117, the air intake(s) 123 and 125, and exhaust port(s) 113, create a vortex of air movement around the cultivated plant held within the chamber(s) 106 and 107. This allows the movement of air from all areas of the chamber around the plant, and encourages a steady flow of fresh, cool air drawn in from the bottom of chamber(s) 106 and 107, toward the top of the chamber(s) 106 and 107, where hotter air is then released through exhaust port(s) 113.

As mentioned above, each of chamber(s) 106 and 107 are preferably substantially waterproof and air tight (with the exception of the filtered openings of intakes 123 and exhaust port(s) 113 and "grommett" for electricity access to an outlet 110). To aid in sealing and waterproofing, each of the opaque walls of chamber(s) 106 and 107 are preferably composed, at least in part, or lined with a waterproof material, such as fiberglass or plastic. Similarly, port(s) 105 also are preferably composed of a waterproof, air-tight, and transparent material (e.g., being composed of fiberglass, PVC or other suitably dense plastic-derived materials).

To provide light and fuel photosynthesis for a plant, such as but not limited to an autoflowering cannabis plant, an array 129 of LED light(s), such as the examples shown by 131, are within, or abut, each of chamber(s) 106 and 107—preferably, at the top of each chamber, as pictured. In some embodiments, the LED lights 131 are positioned at a distance from the floor of each chamber such that the average height of a mature autoflowering cannabis (or of a particular strain or variety of mature, autoflowering cannabis) within a pot in which it is planted, and placed on the floor of chamber(s) 106 and 107 causes the top of the canopy of the plant to be about 3 to 4 inches away from the closest, an average or any LED, or 6 inches away from the closest, an average or any LED, and more preferably, exactly between 3 to 4 inches or 6 inches away. However, other distances may also, or alternatively, be implemented in some embodiments of the invention. For example, in some embodiments, the height of the internal chamber(s) 106 and 107 are 50 inches, or about 50 inches. In some embodiments, the depth and width of chambers 106 and 107 are 25 inches, or about 25 inches. Preferably, as many as between 60 and 150 individual LEDs may be used in an array and within one chamber(s) 106 and 107. These LED bulbs can be configured to cover a variety of light spectrums, including but not limited to UV and UV-B which are optimal for inhibiting unwanted microbes such as mold and mildew. Preferably these will be wavelengths conducive to high PAR as productions of both chlorophyll A and chlorophyll B. Other frequencies used to repel insects may also be employed.

A wide variety of LED components may be used in accordance with the present disclosure. However, in some embodiments, the LEDs create a relatively high level of PAR for plants in general. More preferably, a high level of PAR for autoflowering cannabis, in comparison with non-PAR radiation emitted by the LEDs 129. In preferred embodiments, a PAR of at least 1,500 micromoles is created by the selected LEDs and their power source. In even more preferred embodiments, a PAR of between 1,800 and 2,000 is created by the selected LEDs and their power source(s). Also, the ratio of PAR to wattage is preferably high with a wattage of just 100 to 200 for all of the LEDs of each of LED array(s) 129, resulting in lower heat despite higher growth rates caused by the high PAR within each chamber(s) 106 and 107. In some embodiments, full spectrum LEDs are used, and the LEDs may be coupled with 3 or 5-watt lenses. Alternatively, each LED may be programmed to any wattage between 1 watt and 10 watts. These LEDs are then coupled with lenses, which are often arranged at an angle to ensure that light reaches the lower branches of any incorporated plant In some embodiments, the LED array(s) 129 may be suspended (e.g., by winch-adjustable cables, chains, ropes or struts) above the floor of chamber(s) 106 and 107, and above the top of the canopy of a plant being cultivated within them. By adjusting the height of the LED array 129, a user can track and optimize the distance of the LED array 129, to be within the distance ranges set forth above at all times. Also preferably, a clip or other attachment device is also suspended from the ceiling of each of chambers 106 and 107, which allows a user to suspend and invert a fully cultivated plant, for curing before harvest.

In some embodiments, each chamber 106 and 107 comprises condition monitoring hardware, such as chamber observation camera(s) 133, and meter(s) or sensor(s) 135. In some embodiments, camera(s) 133 and sensor(s) 135 are wired for communications with a computer system such as a personal computer, mobile phone, or other internet-enabled electronic device. Preferably these devises are adapted for observation and management (e.g., through a graphical user interface ("GUI") by a user of the system. In some embodiments, the computer system includes a network of computers, such as the Internet, allowing a user to observe cultivation and other conditions within each chamber(s) 106 and 107 remotely (e.g., from their smartphone or home computer) using a software application adapted to receive data from the camera 133 and meter(s) or sensor(s) 135. In some embodiments, meter(s) 135 comprise one or more thermometer(s), hydrometer(s), humidity meter(s), and/or barometer(s). In some embodiments, and in methods such as those set forth below, in reference to FIG. 2, this monitoring hardware can be used to aid the user in maintaining an optimum room temperature of between 65 and 80 degrees Fahrenheit (a range of between 70 to 78 being ideal), and a humidity of between 35 and 55 percent (and not above 60 percent). A user can also remotely monitor the degree of growth, height, and development phase of the cultivated plant.

Preferably, the system in accordance with the present disclosure 137 is styled as a piece of furniture, with the appearance of a real-wood finish and/or other furnishing appointments, such as handled drawers 137 and legs 139. Legs 139 also provide clearance for said system, permitting air to abut and flow through lower air intake(s) 123. Unconventional furnishing appointments, including "cosmetic" drawers and a rear access door (not pictured) to add and remove plants from the chamber(s) 106 and 107, are also preferably included.

Figure 2:
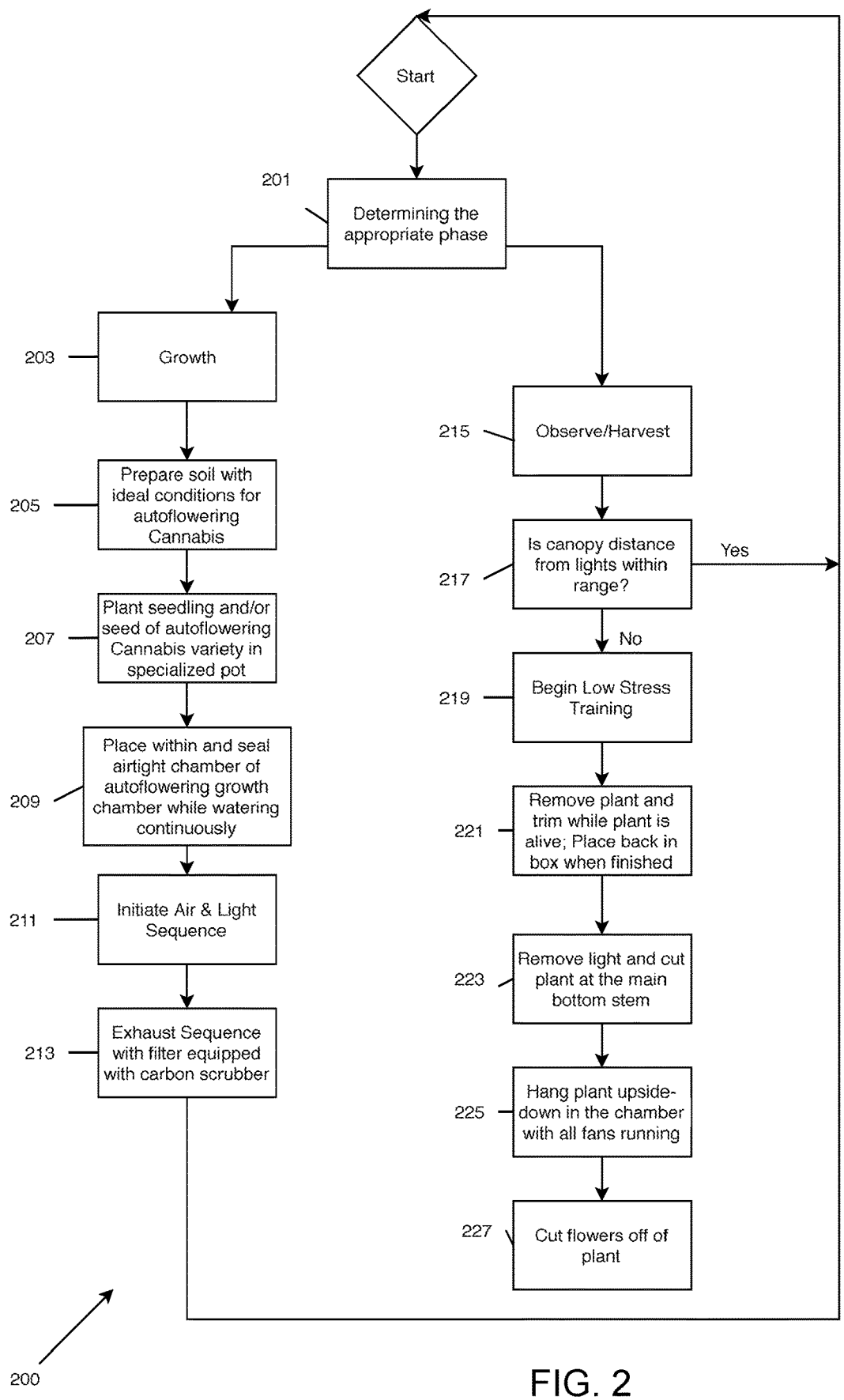
FIG. 2 is a process flow diagram, illustrating exemplary steps for cultivating autoflowering cannabis with the aid of a system, such as the system set forth in reference to FIG. 1, in accordance with aspects of the present invention.

FIG. 2 is a process flow diagram, illustrating some exemplary steps 200 for methods of cultivating autoflowering cannabis with the aid of a system, such as system 101, set forth in reference to FIG. 1, in accordance with aspects of the present invention.

It should be understood that the steps in accordance with the methods set forth in this application may be conducted in a number of alternative orders, repetitions, partial repetitions, instances and combinations with other steps set forth in the application and other steps known or unknown in the art. The group of methodological steps set forth in this application are exemplary only. Also, the steps set forth herein may be executed by a single user of the method, or a group of users, which may be human or non-human users (e.g., by robotic actuation or by another combination of computer hardware or software). It should also be understood that the method set forth herein is executed with the aid of a number of real-world hardware devices, such as the devices set forth elsewhere in this application. This method is not, and should not be construed as merely a group of mental steps.

Beginning with step 201, a user first determines what phase, and resulting grouping within that phase, of the methods will be executed following step 201. If the user wishes to enter a growth phase of the methods, the user will proceed to step 203, entering the growth phase of the methods. If not, the user will proceed to step 215, entering the observation and/or harvesting phase of the method. In a preferred embodiment, the user selects the growth phase if, and only if, the canopy of a plant cultivated in system 101 is more than 3 inches (or, in some embodiments, 4 inches) from any, all or an average of LED lights 129 within the growth chamber(s) 106 and 107. In other embodiments, the user may select the harvest phase if the canopy of a plant cultivated in system 101 is less than 3 inches (or, in some embodiments, 4 inches) from any, all, or an average of LED lights 129 within the growth chamber(s) 106 and 107. In still other embodiments, a user may select the growth phase based on any number of factors indicating whether a plant within chamber(s) 106 and 107 is a minimum height, or has or has not reached a mature, flowering stage (e.g., no buds have yet formed) and vice versa, for selecting the harvest or observation phase in step 215. In those embodiments, if the plant has reached a minimum height, or has exhibited other characteristics of a mature plant (e.g. budding or flowering), the user may select step 215, and the observation/harvesting phase. If not, the user may proceed to step 213, entering the growth phase of the methods.

Assuming that, in step 201, the growth phase has been selected by the user, the user proceeds to step 203, entering the growth phase of the method. Proceeding then to step 205, the user next prepares a soil with components suitable for a plant to be cultivated within chamber(s) 106 and 107. As explained above, the soil has an approximately neutral pH, or a slightly basic pH or, in some embodiments, a slightly acidic pH. Preferably, the soil has a core pH of 6.2 to 6.8, with 6.8 being a maximum, and is certified organic by a reliable authority, such as the California Department of Food and Agriculture ("CDFA"). Such a soil may also be prepared commercially, as for conventional plants or for cannabis or autoflowering cannabis, and subsequently purchased by a user once legal to do so in a user's jurisdiction. In some embodiments, specialized nutrients, such as microbes to enhance the cultivated plant's immune system, worm castings, perlite, bat guano, fish and crab meal, sandy loam, and peat moss, may also be added and mixed into the soil.

Proceeding to step 207, the user then plants a seed, seedling, or other immature plant, within the soil, and within a pot to be placed at the bottom of the chamber(s) 106 and 107. Other forms of plants, aside from autoflowering cannabis, may instead be placed in a hydroponic or aeroponic substrate, but autoflowering cannabis is preferably potted, in accordance with aspects of the present invention.

The user next proceeds to step 209, in which the user places the potted immature seed or plant into the chamber(s) 106 or 107. For example, the user provides water to the immature plant or planted seed (preferably, about ½ gallon of purified water per day). Once in place at the bottom of the chamber, the user then closes and thereby seals the airtight and watertight aspects of the chamber and system 101. However, the user re-access the plant through the door periodically to provide water and other nutrients, as discussed above. Preferably, the pH of water provided to the cultivated plant is between 5.5 to 5.7.

Proceeding to steps 211 and 213, the user next initiates the light and air circulation subsystems, as discussed above, in reference to FIG. 1. In some embodiments, the user may lower an array of LEDs within the chamber to attain the desired distances of the LED(s) from the canopy of the cultivated plant, as set forth above.

The user may then return to the starting position of the methodology. If, at step 201, the user determines that the observation and harvesting phase should begin, the user proceeds to step 215, in which the user observes the maturity of the plant, to determine whether it is sufficiently mature to harvest, in step 217. This may be done through observation of characteristics of the plant, and/or by the height of the plant (or distance from the ceiling) or distance from the LED array 129 (if in a fixed or highest position permitted within the chamber). In step 219, the user employs low stress training. In step 221, the user removes and trims the plant, and subsequently places it back in the box. Three days later, in step 223, the light is removed and the plant is cut at the main bottom step. In step 225, the plant is hung upside-down in the box with all fan running for a period of 3-4 days. The flowers from the plant are then harvested in step 227. It is understood that when an element is referred hereinabove as being "on" another element, it can be directly on the other element or intervening elements may be present therebetween. In contrast, when an element is referred to as being "directly on" another element, there are no intervening elements present.

Moreover, any components or materials can be formed from a same, structurally continuous piece or separately fabricated and connected.

It is further understood that, although ordinal terms, such as, "first," "second," and "third," are used herein to describe various elements, components, regions, layers and/or sections, these elements, components, regions, layers and/or sections should not be limited by these terms. These terms are only used to distinguish one element, component, region, layer and/or section from another element, component, region, layer and/or section. Thus, a "first element," "component," "region," "layer" and/or "section" discussed below could be termed a second element, component, region, layer and/or section without departing from the teachings herein.

Features illustrated or described as part of one embodiment can be used with another embodiment and such variations come within the scope of the appended claims and their equivalents.

Spatially relative terms, such as "beneath," "below," "lower," "above," "upper" and the like, are used herein for ease of description to describe one element or feature's relationship to another element(s) or feature(s) as illustrated in the figures. It is understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device can be otherwise oriented (rotated 90 degrees or at other orientations) and the spatially relative descriptors used herein interpreted accordingly.

Example embodiments are described herein with reference to cross section illustrations that are schematic illustrations of idealized embodiments. As such, variations from the shapes of the illustrations, for example, of manufacturing techniques and/or tolerances, are to be expected. Thus, example embodiments described herein should not be construed as limited to the particular shapes of regions as illustrated herein, but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

As the invention has been described in connection with what is presently considered to be the most practical and various embodiments, it is to be understood that the invention is not to be limited to the disclosed embodiments, but on the contrary, is intended to cover various modifications and equivalent arrangements included within the scope of the appended claims. Although specific terms are employed herein, they are used in a generic and descriptive sense only and not for purposes of limitation.

This written description uses examples to disclose the invention, including the best mode, and also to enable any person skilled in the art to practice the invention, including making and using any devices or systems and performing any incorporated methods. The patentable scope of the invention is defined in the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

In conclusion, herein is presented a system and method for unusually high yield per plant of autoflowering cannabis. The disclosure is illustrated by example in the drawing figures, and throughout the written description. It should be understood that numerous variations are possible while adhering to the inventive concept. Such variations are contemplated as being a part of the present disclosure.

What is claimed is:

1. A system for aiding the cultivation of autoflowering cannabis, comprising:
   a chamber having a front end, a rear end, a top side, a bottom side, a right side, a left side, and an impermeable median,
     wherein the impermeable median extends from the front end to the rear end and the top side to the bottom side,
     wherein the chamber has at least one passive air intake proximate a bottom of the chamber and draws air in from outside the chamber, at least one air exhaust port, each of the at least one passive air intake and the at least one air exhaust port being equipped with a carbon-based filter and the at least one passive air intake having an anti-pest mesh;
   a first subchamber bounded by the left side, the top side, the bottom side, the rear end, the front end, and the impermeable median, the first subchamber comprising a first fan array having three fans and a first fan air intake, and a second fan array having three fans and a second fan air intake, the first fan array partially disposed on the rear side and the left side, the second fan array partially disposed on the impermeable median and the rear side a second subchamber bounded by the right side, the top side, the bottom side, the rear end, the front end, and the impermeable median, the second subchamber comprising a third fan array having three fans and a third fan air intake, and a fourth fan array having three fans and a fourth fan air intake, the first fan array partially disposed on the rear side and the impermeable median, the second fan array partially disposed on the rear side and the right side,
     wherein the bottom side is configured to support at least one autoflowering cannabis plant; a light array, comprised of a plurality of light-emitting diodes, the plurality of light-emitting diodes having a first portion of light-emitting diodes and a remainder portion of light-emitting diodes, the first portion of light-emitting diodes disposed within the first subchamber, the remainder portion of light-emitting diodes disposed within the second subchamber, the light array being proximate to the top side and configured to radiate light towards the bottom side, wherein the at least one passive air intake is located proximately to and below the first fan air intake, the second fan air intake, the third fan air intake, or the fourth fan air intake; and
   wherein the fan arrays are configured to create a vortex of airflow within the chamber and around a plant, when present, drawing air in the bottom and releasing air towards the top of the chamber.

2. The system of claim 1, wherein the light array produces light within the photosynthetically-active radiation ranges of autoflowering cannabis.

3. The system claim 2, wherein the light array produces light within the photosynthetically active radiation ranges of autoflowering cannabis to a greater degree than light outside the photosynthetically active radiation ranges for autoflowering cannabis.

4. The system of claim 3, wherein each of the plurality of light-emitting diodes is configured to emit light having wavelengths of 430 and 662 nanometers.

5. The system of claim 3, wherein each of the plurality of light-emitting diodes is configured to emit light having wavelengths of 452 and 652 nanometers.

6. The system of claim 5, wherein the light array creates photosynthetically active radiation of at least 1,500 mol $m^{-2}s^{-1}$.

7. The system of claim 6, wherein the light array draws between 100 and 200 Watts of power.

8. The system of claim 7, further comprising condition monitoring hardware, located within the chamber.

9. The system of claim 8, wherein the condition monitoring hardware is selected from the group consisting essentially of: at least one chamber observation camera, a moisture sensor, at least one thermometer, at least one hydrometer, and a barometer.

* * * * *